United States Patent [19]

Heinemann et al.

[11] Patent Number: 4,524,038

[45] Date of Patent: Jun. 18, 1985

[54] METHOD OF MAKING A VIBRATION-RESISTANT ELECTRICAL COMPONENT AND CONNECTION LEAD COMBINATION, PARTICULARLY EXHAUST GAS COMPOSITION SENSOR

[75] Inventors: Wolfgang Heinemann, Weissach; Rainer Noack, Bietigheim; Helmut Weyl, Schwieberdingen, all of Fed. Rep. of Germany

[73] Assignee: Robert Bosch GmbH, Stuttgart, Fed. Rep. of Germany

[21] Appl. No.: 424,536

[22] Filed: Sep. 27, 1982

[30] Foreign Application Priority Data

Dec. 19, 1981 [DE] Fed. Rep. of Germany ....... 3150435

[51] Int. Cl.³ .............................................. B28B 23/00
[52] U.S. Cl. ........................................ 264/61; 29/854;
29/855; 29/856; 264/62
[58] Field of Search ................ 264/63, 61, 177 R, 60,
264/62; 29/854, 855, 856

[56] References Cited

U.S. PATENT DOCUMENTS

| 2,750,657 | 6/1956 | Herbert | 264/61 |
| 3,405,382 | 10/1968 | Wright | 29/854 X |
| 3,968,193 | 7/1976 | Langstron | 264/61 |
| 4,374,457 | 2/1983 | Wiech | 264/63 |

FOREIGN PATENT DOCUMENTS 2526340 12/1976 Fed. Rep. of Germany .

*Primary Examiner*—Jan Silbaugh
*Attorney, Agent, or Firm*—Frishauf, Holtz, Goodman & Woodward

[57] ABSTRACT

To manufacture a vibration-resistant, shock-resistant electrical connection on a ceramic substrate (11) having an electrically conductive layer (12) applied to a surface (13, 19) thereof, a groove or channel-like depression (16, 20) is formed in the surface, preferably also including a through-bore (18), into which a conductor (17) is placed. The space between the conductor and the groove, the through-bore, if provided, and an extending groove at the other surface (19) of the substrate is filled with a sinterable mass (21), preferably a cermet, containing a metal which is compatible with the metal of the conductor wire (17), both for example containing platinum. As a starting material, the plate with the grooves therein is extrusion-pressed, pre-sintered at a low temperature to give it form stability, then the electrode (12) is applied, then the electrical conductor (17) and the cermet is applied and then the entire sub-assembly is fired to sintering temperature, e.g. about 1500° C.; if desired, a further protective coating (22) of magnesium spinel may be plasma-sprayed on. Due to shrinkage of the ceramic components, the wire (17) will be securely held in position in the groove, and the cermet additionally forming an electrical connection between the wire and the substrate (11). For additional strain relief, the groove can be undulating (FIG. 3).

24 Claims, 3 Drawing Figures

METHOD OF MAKING A VIBRATION-RESISTANT ELECTRICAL COMPONENT AND CONNECTION LEAD COMBINATION, PARTICULARLY EXHAUST GAS COMPOSITION SENSOR

Reference to related patents assigned to the assignee of the present invention, the disclosure of which is hereby incorporated by reference: U.S. Pat. No. 4,300,990, MAURER.

Reference to relates published state of technology: German Patent Disclosure Document DE-OS No. 25 26 340; U.S. Pat. No. 3,616,413, Rechner; and U.S. Pat. No. 4,157,282, Riddel.

The present invention relates to a method of manufacturing an electrical circuit component and connection lead combination, and more particularly to a method which permits such manufacture in which the component includes a sinterable, ceramic substrate which may be brittle, especially a substrate including aluminum oxide, zirconium dioxide, or the like, and suitable, for example, as an exhaust gas composition sensor or a component thereof.

BACKGROUND

It has previously been proposed to make electrical components which have a thin-walled substrate of ceramic material or the like, and on which an electrically conductive layer is adhered to one side by forming a metallic connection with a wire to the electrode, and additionally providing the substrate, the layer-electrode and the wire with a bonding mass or cement, to secure the assembly together and form a unitary combination. A process and a structure in accordance with this method is disclosed in the referenced U.S. Pat. No. 3,616,413. It has been found that if the metallic layer or electrode is extremely thin, and the carrier, itself, is very thin, making the electrical connection is costly and difficult, particularly under mass production conditions. It has also been found that electrical connections made this way, when subjected to vibration, shock or the like, which may be encountered if components with such connections are installed in automotive vehicles, may lead to failures. When exposed to exhaust gases from an internal combustion engine—in other words, when exposed to high temperatures—and shock or vibration, the lifetime of combinations, assemblies or connections made in accordance with the known process is subject to improvement.

It has previously been proposed to utilize rivet connections or the like to interconnect layers, for example forming electrodes or electrically conductive tracks on carriers. Rivet connections, it has been found, are not suitable for brittle substrates which are subjected to shock or vibrations; they are difficult to manufacture under mass production conditions, particularly with brittle ceramic substrates which tend to crack upon riveting or eye-letting. The reject rate, under mass production conditions, is high.

It has also been proposed—see the referenced German Patent Disclosure Document DE-OS No. 25 26 340—to use solder or spring clamp connections. Such spring clamp connections are suitable for laboratory or casual or test measurements; for combination as permanent connections in automotive environments, they are not suitable and, further, too costly.

THE INVENTION

It is an object to provide a method of making an electrical component, based on a ceramic substrate or carrier, typically of plate form, and a connection lead extending therefrom, which is simple, reliable, and suitable for mass production conditions, while providing a connection which is secure and permanent even if the component is subject to shocks, vibration, and wide temperature swings.

Briefly, a substrate carrier, for example in plate form, is made of a ceramic material, in soft state. A surface of the carrier, in the region where an electrical connection lead is to be applied to a layer electrode, is formed with a groove or channel-like depression in the surface. The groove, thus, will be delimited and defined by groove walls. In accordance with a feature of the invention, a through-hole may also be formed extending through the thickness of the plate. The groove may, for additional strain relief, be formed in undulating shape. The thus pre-formed, still soft ceramic element is pre-sintered, so that it will be form-stable and can be handled. A layer-electrode, which may be a conductive track, an electro-chemically responsive electrode, a resistance track, or the like, is then applied to the surface. A connecting wire, which has slightly smaller diameter than the width and preferably also the depth of the groove, is placed or laid longitudinally in the groove between the walls thereof, and a sinterable bonding material is introduced in the clearance space between the wire and the groove walls surrounding the wire. The wire and the bonding material thus extend essentially parallel to the surface of the groove. In accordance with a preferred feature of the invention, the bonding material is a conductive cermet, that is, a metal-ceramic composition which is sinterable. The sub-assembly thus obtained is then finish-sintered. Upon finish-sintering, the dimensions of the plate will change, that is, sintering involves shrinkage. Upon shrinking of the substrate plate, the connecting wire will be tightly gripped within the groove, while the sinterable bonding material additionally tightly grips the wire therein and, if made of conductive material, provides an electrical connection, or an additional electrical connection between the wire and the electrode surface.

In accordance with a feature of the invention, the groove terminates in a through-bore, so that the wire can be passed in the groove, through the thickness of the carrier, and then along another groove, continuing in essentially the same direction, the wire then being bent in a generally "figure 2" shape; alternatively, the wire can be hooked through the through-bore, or the through-bore can be omitted. The groove, itself, can be made of undulating shape. The step of introducing the cermet can easily be done under mass production conditions by dripping-in a small quantity of the material. When used as an exhaust gas sensor, the cermet preferably employs a noble metal, for example platinum, and the ceramic substrate material is zirconium dioxide, which also forms the ceramic for the cermet.

In accordance with a preferred feature of the invention, the carrier is a small plate made of zirconium dioxide, about 8 mm wide, 1 mm thick, and 1–3 cm long—see, for example, the referenced U.S. Pat. No. 4,300,990, MAURER. Rather than using a carrier made of zirconium dioxide, other materials which are capable of being sintered can be used, for example aluminum oxide. The present invention is not limited to carriers made of zirconium dioxide or aluminum oxide, nor to oxygen sensors to determine the oxygen content in exhaust gases. The present invention is applicable, in general, to any electronic component having a substrate of a material capable of being sintered, and having an electrically conductive layer on the surface thereof. The method of applying the electrically conductive layer can be in accordance with any well known system, for example screen printing, stamp-on printing, spraying, or the like. The electrically conductive layer can be made of various metals, for example platinum, or a platinum metal, or may use other suitable and desired metals, or may utilize cermets. The electric layer, for example, can be about 10 micrometers thick and 2 mm wide, to form an electrically conductive track, for for example for a layer-like resistance heater on the carrier substrate 11.

The method has the advantage that a wire connection to a thin layer electrode on a brittle substrate can be made which is essentially vibration and shock-resistant, and thus suitable for the rough operating environments of automotive vehicles; additionally, it is simple and capable of exact reproduction, so that it is suitable for mass production application. The method is inexpensive; and, in accordance with a preferred embodiment, strain relief to the wire connection can readily be built into the final structure without any essential change in the method, or introducing any significant cost. Since the wire extends, in its groove, essentially parallel to the surface of the substrate, tension on the wire will not readily separate the wire from the groove and hence from the electrical connection to the underlying thin layer electrode.

DRAWINGS

DETAILED DESCRIPTION

Figure 1:
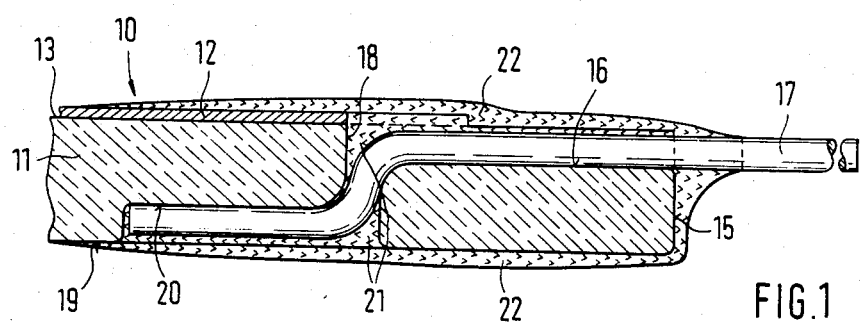
FIG. 1 is a schematic cross section through the connecting portions of a ceramic oxygen sensor substrate, including the connecting wire.

The invention will be described in connection with an oxygen sensor of the type described in U.S. Pat. No. 4,300,990, MAURER, assigned to the assignee of the present application, the disclosure of which is hereby incorporated by reference. The substrate carrier is a plate of zirconium dioxide, about 1 mm thick and about 8 mm wide. It is not necessary for purposes of the present invention that the substrate 11 is made of zirconium dioxide; any material capable of being sintered, such a aluminum oxide may be used. The present invention, as noted, is also applicable to forming a connection in which any sinterable substrate has an electrically conductive layer thereon which is to be connected to a wire.

Electrode layer or track 12 is applied to one major surface 13 of the substrate or plate 11. The plate or substrate is pre-sintered, that is, has been passed through a firing step at a temperature which is below sintering temperature, but sufficient to provide the substrate plate applied, for example, on a carrier tray or holder, with sufficient rigidity and strength so it can be handled and which permits application of the electrically conductive layer 12 on the surface 13. Layer 12 can be applied in accordance with any well known procedure, for example by screen printing. If the element is to be used as an oxygen sensor, the layer 12, if used as an electrode, may include a platinum metal, platinum, or other metals, or cermets, suitable for the purpose; the conductive layer may, for example, have a thickness of 10 micrometers and a width of 2 mm. The conductive layer 12 may, also, be used for different purposes, for example as a layer-like resistance element, or may form a conductive connecting track to such a layer-like resistance element or to a sensing electrode. The electrically conductive layer 12, which is securely bound to the carrier 11 and sintered thereto after a final sintering step, terminates at an edge line 14. Edge line 14 is set back from the edge 15 of the carrier 11 by some distance, in accordance with the above example, preferably about 2 mm. Carrier 11 is shown as a flat plate; it may, however, also be bowed or bent, the end portion of the tube, or the like.

In accordance with the present invention, a channel-like depression or duct or groove 16 is formed in the surface 13. Groove 16 starts at the edge line 15 of the plate and extends at least up to and preferably in the region of the electrically conductive layer 12. The width of this groove is so dimensioned that a metallic connecting wire 17 is closely retained therein, with just a slight amount of clearance, however, A fairly tight fit is desirable. The wire 17 may, for example, be a platinum wire with a diameter of 0.25 mm. For such a platinum wire, a groove 16 with a width of 0.26 mm is suitable. The depth of the groove, preferably, is at least as deep as the diameter of the wire, or slightly more—in the present example preferably about 0.3 mm.

The dimensions given above are for the pre-sintered but not finish-sintered substrate 11. The reason for this will appear below. Of course, other dimensions may be suitable.

The wire 17 may have any desired cross section; for example, and as shown, it may be circular, but it may, also, be formed as a flat ribbon, with a square cross section, or may be polygonal.

In accordance with a feature of the invention, and as shown in FIG. 1, a through-bore 18 is formed at the end of the duct 16, extending transversely to the surface 13. It need not extend at angle of 90°; any other suitable angle may be used, for example of an angle of 45°. Assuming, again, a connecting wire 17 with a diameter of 0.25 mm, an internal diameter of the opening 18 of 0.3 mm in the pre-sintered carrier 11 is suitable. The through-bore terminates at the second side 19 of the carrier 11, and there merges into a second groove 20 which, for example, may have essentially the same dimensions as the groove 16. The end portion of the wire 17 in the groove 20 is carried therethrough for a length of about 2 mm. In accordance with a preferred feature of the invention, the end portion of the wire 17 and the portion in the groove 16 are in at least approximate alignment, and the groove 20 extends in the same direction as the groove 16. This is not a necessary requirement, however, and for other applications, the groove 20 in the second side 19 of the carrier or substrate may extend in another direction than the groove 16, for example at right angles thereto, or backwards, so that the wire 17 will be bent over itself in hook-shaped configuration.

In accordance with a preferred feature of the invention, the grooves 16, 20 as well as the intersections of the grooves with the through-bore 18 are rounded, as seen in FIG. 1, and to prevent sharp edges and the possibility of fissures at the transition between square corners.

When making the body 11, pasty ceramic material is extruded from a form press which can be so shaped that, in the one extrusion and pressing step, the opening 18 as well as the grooves 16, 20 are formed at the same time. After making the preformed or pre-profiled carrier 11, it is subjected to a firing step in which it is pre-sintered. This firing step is carried out at a substantially lower temperature than the final firing or sintering temperature; the temperature required is only that which gives the starting block or plate 11, with the grooves and opening 18 formed therein, sufficient strength and stability to permit carrying out subsequent operating steps thereon. A suitable pre-sintering temperature is 1200° C.

The pre-sintered carrier 11, then, has the electrically conductive layer 12 applied thereto; if desired, other layers can be applied to the body 11, to form a complete electronic component 10, for example the oxygen sensor of the referenced U.S. Pat. No. 4,300,990, MAURER. The next two steps are placing of the connecting wire 17 by threading the wire 17 through the hole 18, placing it in the grooves 16, 20, and introducing an electrically conductive, sinterable bonding or cement mass 21 thereinto. Mass 21, for example, can be introduced by placing drops thereon, or dripping a slip, or suspension of a cermet into the groove 16, and through the opening 18, where it will also flow into the groove 20. A mass 21, which is also suitable for electrical connection between the connecting wire 17 and the electrically conductive layer 12, and which is particularly suitable, is a noble metal cermet, applied in form of a suspension, for example containing 50% platinum and 50% zirconium dioxide (by volume) suspended, as well known, in any suitable suspension medium which will be evaporated or become volatile upon sintering of the element 10. Rather than using platinum, other metals may be used, and other ceramic materials than zirconium dioxide may be used, for example aluminum oxide. Mention should be made that the steps of "placing of the connecting wire" and "introducing a mass" will function in a reverse sequence as well.

In the next method step, the carrier 11, the electrically conductive layer, any other layers which may have been applied to the carrier 11, if any, and the connecting wire 17, as well as the bonding compound 21 are sintered together. The sintering step is carried out in a furnace at a temperature of, for example, about 1500° C. In accordance with a feature of the present invention, use is made of the shrinkage of the ceramic material which, during the sintering step, will shrink by about 20%, leading to tight clamping of the connecting wire 17 within the grooves 16, 20 and the opening 18. Additionally, the connecting element 17 is securely held in position by the now finish-sintering bonding substance or mass or cement 21 within the carrier 11; simultaneously, the connecting element 17 is electrically connected to the electrically conductive layer 12.

The connection element 17 which extends beyond the end surface 15 of the carrier 11, for example by about 5 mm, can then be readily connected to other electrical components by any suitable method, for example by soldering, welding, clamp or push connections, or the like, or otherwise connected to a further connection wire or cable. The wire 17 is securely retained in position against strain or pulling forces, and also securely retained within the plate with respect to vibration and shocks. This retention is effective also at high operating temperatures which, for exhaust gas sensors, may reach close to 1000° C. while, before having reached operating temperature, the element may have been exposed to temperatures well below freezing.

The angled-off or offset course of the connecting wire 17 in the grooves 16, 20, and the through-bore 18 provides for efficient and highly effective strain relief. For installations in which such high performance strain relief is not required, some manufacturing time and hence cost can be saved by omitting the groove 20 or even the through-bore 18.

Figure 2:
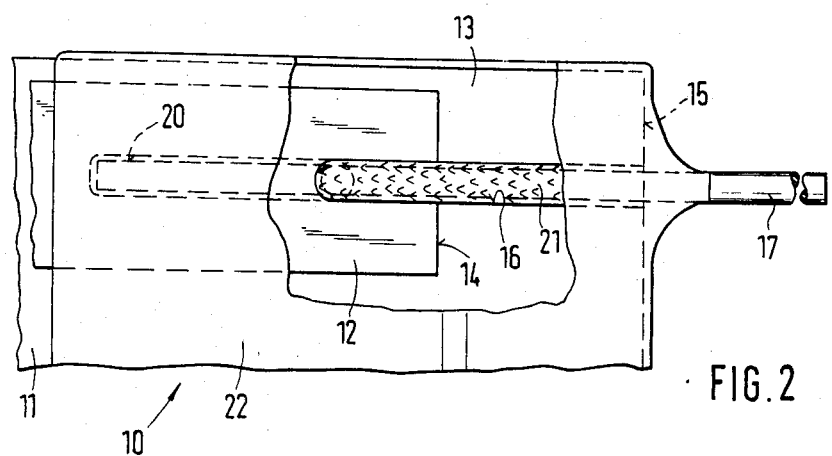
FIG. 2 is a top view of the connecting portion of FIG. 1, with part of a top covering layer removed.

In accordance with a feature of the invention, the connecting region of the carrier 11 can be further stiffened and positioning of the wire 17 insured by applying an additional insulating layer 22—see FIG. 2—thereover. A suitable application step is to use the well known plasma spraying method. The insulating layer 22 may, for example, be made of magnesium spinel. Depending on the particular embodiment and shape of the connecting region used, the layer 22 can be applied over the grooves 16, 20, and the through-bore 18—to the extent not filled by the sintered cermet 21—at the first major side 13 and/or at the second major side 19 of the carrier 11. In accordance with a preferred embodiment, it may completely surround the carrier 11 and, to some extent, even jacket the free end portion of the connecting wire 17 in part, for example to a length of about 2 mm. Preferably, such an insulating layer 22 of magnesium spinel may have a thickness of between 0.1 mm to 0.5 mm.

Figure 3:
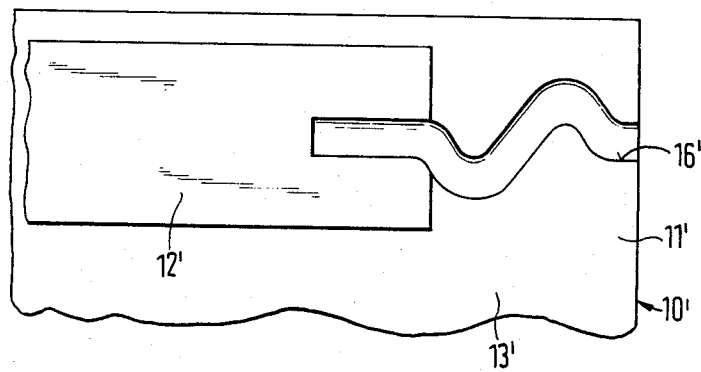
FIG. 3 is a top view similar to FIG. 2, illustrating another embodiment.

Embodiment of FIG. 3: A carrier 11', similar to the carrier 11 of FIG. 2, has a groove 16' on the top side 13' which has zig-zag or undulating shape, and terminates in the region of the electrically conductive layer 12'. For uses where extremes of strain relief are not needed, the undulating or tortuous path of the groove 16' provides a sufficient strain relief for a connecting element or connecting wire placed therein, and not shown in FIG. 3 for simplicity of the drawing. Such a connecting wire, similar to wire 17 but, for example, pre-formed to fit into the undulating groove 16', is easily made and pre-shaped, and thus saves forming the through-bore 18 (FIGS. 1 and 2) and the second groove 20 in the second major side 19 of the carrier plate 11. The electrical layer 12' may extend within the groove 16', so that electrical connection by direct contact between a wire placed in the groove 16' and the layer 12' is insured.

The method of making the structure of FIG. 3 is similar to that described in connection with FIGS. 1 and 2, the manufacturing steps being identical. The groove 16' is pre-formed when making the plate 11' in the forming press.

For some applications, both major sides 13 and 19 will have electrodes similar to electrode 12 applied thereto, which are to be separately connected to separate connecting wires 17. For such applications, it is desirable to laterally offset the respective wires 17, so that they will not be in vertical alignment among each other. Such offset renders the overall structure 10 or 10', respectively, less subject to breakage.

The connecting portion can be readily fixed in the carrier 11 additionally by soldering or brazing after the carrier and the electrically conductive layer 12, and such other layers as may be present, is already finally sintered. If such an additional connection is used, it is desirable to secure the position of the wire 17 by a through-bore 18 and, further, to insure alignment and proper positioning, by also forming the groove 20 in the second side 19 of the carrier 11. An additional insulating layer 22, also and desirably, is further applied over the entire assembly.

The insulating layer 22 can also be used, of course, if the carrier 12 and the electrically conductive layer are only formed with a through-bore 18 and a groove 16, so that the connecting wire 17 is essentially hooked into the carrier 11. The insulating layer 22 will then have its previously described protective and supportive function. Preferably, the connecting wire 17 is further connected to the layer 12 by soldering, brazing, or the like, and the insulating layer 22 is then applied by plasma-spraying on the connected and soldered region, at least on the side 13, and preferably also on the side 19, and surrounding the edge portion 15 of the carrier, including a small jacketing extension over the connecting wire 17, as shown in FIG. 1.

The connecting wires 17, preferably, are made of platinum, nickel, an aluminum metal alloy, tungsten; other suitable materials may be used.

In some structures, a conductive layer similar to the layer 12 can be applied to the second major surface portion 19. In such structures, the connecting element 17, of course, can be electrically connected to the conductive layer on the second surface portion 19 as well. Thus, if layer 12, for example, forms a resistance heater connection applied to the top surface 13 of the structure 11, a similar resistance heater connection can be applied to the second surface 19, connected in parallel with the layer 12, a second terminal then being provided at a laterally offset position for return flow of current from the respective resistance elements on the respective sides 13, 19 of the carrier. Thus, two securely adhering conductive layers 12 can be electrically connected to a single conductor 17, or only one such layer on one side, as desired.

Various changes and modifications may be made, and features described in connection with any one of the embodiments may be used with any of the others, within the scope of the inventive concept.

We claim:

1. Method of making an electrical component which comprises
   a substrate (11, 11') of brittle, sinterable material having the characteristic of shrinking upon sintering and having an exposed surface (13, 19);
   a layer electrode (12, 12') applied to said exposed surface;
   an electrical connection wire (17) electrically connected to said layer electrode and mechanically retained on the substrate;
   wherein a bonding mass is provided, securing the connecting wire to the substrate and retaining said wire thereon,
   comprising, in accordance with the invention, the steps of
   forming the substrate (11, 11') in unsintered state;
   forming the surface (13, 19) of the substrate in the region of the connection of the layer electrode (12, 12') and the connection wire (17) with a channel-like depression or groove (16, 16') extending essentially parallel to said surface, the groove being defined and positioned between groove walls;
   pre-sintering the so formed substrate to render the substrate form-stable;
   applying said layer electrode (12, 12') to said surface (13, 19);
   positioning the connection wire (17) longitudinally within said groove (16, 16') and essentially parallel to said surface, the diameter of said connection wire being just slightly smaller than the width of the groove to leave a small clearance space between the longitudinally positioned and opposed groove walls;
   introducing an electrically conductive sinterable bonding material (21) into the clearance space between the groove walls and the connection wire, said sinterable bonding material surrounding and embedding the connection wire therein to form a sub-assembly comprising the substrate (11, 11'), the layer electrode (12, 12') thereon, the connection wire (17) within the groove (16, 16') and the sinterable bonding material (21) in said groove;
   and then finish-sintering said sub-assembly while shrinking the substrate and the sinterable bonding material to securely hold the connection wire in said groove by clamping of the wire between the groove walls upon shrinkage of the substrate and the bonding material.

2. Method according to claim 1, wherein the groove has a depth slightly deeper than the diameter of the wire, and the sinterable bonding material (21) surrounds said wire at least in the region of connection with the layer electrode (12, 12').

3. Method according to claim 1, wherein the step of forming the substrate in unsintered state includes extruding and pressing a plate-like quantity of said sinterable substrate material while simultaneously forming the channel-like depression or groove.

4. Method according to claim 1, wherein the step of forming said channel-like depression or groove (16, 16') comprises forming the channel-like depression in zig-zag or undulating form;
   and the step of positioning the connection wire comprises pre-forming the connection wire to match the undulation or zig-zag configuration of said groove, and placing said connection wire therein.

5. Method according to claim 3, wherein the step of forming said channel-like depression or groove (16, 16') comprises forming the channel-like depression in zig-zag or undulating form;
   and the step of positioning the connection wire comprises pre-forming the connection wire to match the undulation or zig-zag configuration of said groove, and placing said connection wire therein.

6. Method according to claim 1, including the step of forming a through-opening (18) adjacent the end portion of the channel-like depression or groove (16, 16') extending from said exposed surface of the substrate (11) to an opposite surface thereof;
   and wherein the step of positioning the connection wire (17) comprises introducing said connection wire through said opening (18);
   and the further step of introducing the sinterable bonding material comprises introducing the sinterable bonding material around the connection wire and into the through-opening.

7. Method according to claim 6, including the step of forming an extending channel-like depression or groove (20) at least approximately comparable to said groove (16, 16') in the opposite surface (19) of the substrate (11, 11').

8. Method according to claim 7, wherein the step of forming said extending groove comprises positioning said extending groove in a plane spaced from the plane of said groove (16).

9. Method according to claim 8, wherein said extending groove is in at least approximate alignment with, and extending in the same direction as said groove (16).

10. Method according to claim 7, further including sinterable bonding material (21) positioned in said extending groove, and forming part of said sub-assembly;

and wherein the finish-sintering step includes sintering all the sinterable bonding material on said substrate.

11. Method according to claim 1, wherein said sinterable bonding material comprises a conductive cermet.

12. Method according to claim 11, wherein the step of introducing the sinterable bonding material comprises dripping said bonding material in suspension.

13. Method according to claim 11, wherein said cermet includes a noble metal.

14. Method according to claim 11, wherein said cermet includes a platinum metal.

15. Method according to claim 11, wherein said cermet includes zirconium dioxide as the ceramic component thereof.

16. Method according to claim 1, further including the step of coating at least a portion of the region of said substrate, and including at least a portion of the layer electrode (12, 12') and said connection wire (17) with an insulating layer (22).

17. Method according to claim 16, wherein said insulating layer (22) comprises magnesium spinel.

18. Method according to claim 16, wherein the step of applying said insulating layer comprises plasma-spraying.

19. Method according to claim 16, wherein the step of applying said insulating layer is carried out before finish-sintering;

and wherein the step of finish-sintering includes sintering said insulating layer on the substrate.

20. Method according to claim 1, wherein the substrate (11, 11') essentially consists of zirconium dioxide.

21. Method according to claim 1, wherein said electrically conductive layer comprises at least part of a resistance heating layer.

22. Method according to claim 2, wherein the electrical component is an oxygen sensor, including an electrical connecting wire therefor;

wherein the substrate (11, 11') is a plate-like element consisting, essentially, of zirconium dioxide; and wherein said sinterable bonding material (21) comprises a cermet including zirconium dioxide and a noble metal.

23. Method according to claim 1, wherein the steps of positioning the connecting wire (17) and introducing the sinterable bonding material (21) is carried out in the sequence:

(a) first positioning the connection wire, and (b) then introducing the sinterable bonding material.

24. Method according to claim 1, wherein the steps of positioning the connecting wire (17) and introducing the sinterable bonding material (21) is carried out in the sequence:

(a) first introducing the sinterable bonding material, and (b) then positioning the connection wire.

* * * * *